US006353021B1

(12) United States Patent
Gaglani et al.

(10) Patent No.: US 6,353,021 B1
(45) Date of Patent: *Mar. 5, 2002

(54) STABILIZED COMPOSITION CONTAINING HALOPROPYNYL COMPOUNDS

(75) Inventors: Kamlesh Gaglani, Belle Mead; Meihua Yang, Bridgewater, both of NJ (US)

(73) Assignee: Troy Technology Corporation, Inc., Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 09/566,080

(22) Filed: May 8, 2000

Related U.S. Application Data

(63) Continuation of application No. 08/989,635, filed on Dec. 12, 1997, now Pat. No. 6,059,991.

(51) Int. Cl.[7] ................. A61K 31/27; A61K 31/335; A61K 31/45
(52) U.S. Cl. ............... 514/478; 514/449; 514/389; 514/390; 260/29.6
(58) Field of Search ................ 514/478, 449, 514/389; 424/76.8; 260/29.6 MN

(56) References Cited

U.S. PATENT DOCUMENTS

| 3,660,499 A | 5/1972 | Kobayashi et al. |
| 3,781,417 A | 12/1973 | Weners et al. |
| 3,879,470 A | 4/1975 | Munakata et al. |
| 3,923,870 A | 12/1975 | Singer |
| 3,987,074 A | 10/1976 | Haase et al. |
| 4,018,611 A | 4/1977 | Cramer et al. |
| 4,129,521 A | 12/1978 | Strobel |
| 4,219,480 A | 8/1980 | White et al. |
| 4,259,350 A | 3/1981 | Morisawa et al. |
| 4,276,211 A | 6/1981 | Singer et al. |
| 4,297,258 A | 10/1981 | Long, Jr. |
| 4,323,602 A | 4/1982 | Parker |
| 4,552,885 A | 11/1985 | Gabriele et al. |
| 4,592,773 A | 6/1986 | Tanaka et al. |
| 4,616,004 A | 10/1986 | Edwards |
| 4,639,460 A | 1/1987 | Rose |
| 4,654,434 A | 3/1987 | Lang et al. |
| 4,675,352 A | 6/1987 | Winter et al. |
| 4,710,584 A | 12/1987 | Lang et al. |
| 4,710,854 A | 12/1987 | Yamada et al. |
| 4,719,227 A | 1/1988 | Schade et al. |
| 4,760,148 A | 7/1988 | Seltzer et al. |
| 4,915,909 A | 4/1990 | Song |
| 4,921,966 A | 5/1990 | Steggman et al. |
| 4,945,109 A | 7/1990 | Rayudu |
| 5,047,571 A | 9/1991 | Spang et al. |
| 5,082,722 A | 1/1992 | Gugliemo, Sr. |
| 5,127,934 A | 7/1992 | Mattox |
| 5,144,081 A | 9/1992 | Heywang et al. |
| 5,190,580 A | 3/1993 | Gruening |
| 5,209,930 A | 5/1993 | Bowers-Daines et al. |
| 5,281,645 A | 1/1994 | Chicart et al. |
| 5,342,610 A | 8/1994 | Katoh et al. |
| 5,436,349 A | 7/1995 | Winter et al. |
| 5,468,904 A | 11/1995 | Osawa et al. |
| 5,516,914 A | 5/1996 | Winter et al. |
| 5,554,784 A | 9/1996 | Gruening |
| 5,585,091 A | 12/1996 | Pelzer et al. |
| 5,601,756 A | 2/1997 | Swearengin |
| 6,059,991 A * | 5/2000 | Gagiani et al. ........ 252/182.29 |

FOREIGN PATENT DOCUMENTS

| EP | 0083308 | 7/1983 |
| GB | 2138292 | 10/1984 |

OTHER PUBLICATIONS

Kull, et al., "Mixtures of Quaternary Ammonium Compounds and Long–Chain Fatty Acies as Antifungal Agents," *Applied Macrobiology,* vol. 9, pp. 538–541, 1961.

Gabriel, et al., "Protection of Mildewcides and Fungicides from Ultraviolet Light Induced Photo–oxidation," *J. Coatings Technology,* 56:712, pp. 33–48, May 1984.

* cited by examiner

*Primary Examiner*—Zohreh Fay
*Assistant Examiner*—Brian-Yong Kwon
(74) *Attorney, Agent, or Firm*—Banner & Witcoff, Ltd.

(57) ABSTRACT

This invention is directed to a stabilized biocidal composition which comprises a mixture of at least one halopropynyl compound, and particularly a halopropynyl carbamate fungicide such as IPBC, a UV absorber and an organic epoxide.

21 Claims, No Drawings

STABILIZED COMPOSITION CONTAINING HALOPROPYNYL COMPOUNDS

This application is a continuation application of application Ser. No. 08/989,635, filed Dec. 12, 1997, U.S. Pat. No. 6,059,991.

FIELD OF THE INVENTION

This invention is directed to a biocidal composition, and particularly a composition of a halopropynyl compound containing a mixture of additives for synergistically stabilizing the composition against degradation and discoloration.

BACKGROUND OF THE INVENTION

Both exterior and interior surfaces, substrates of all types and organic compositions and formulations, when exposed to common environmental conditions, e.g. moisture, are prone to attack, discoloration and various kinds of destruction by a variety of species of microorganisms, including fungi algae, bacteria and protozoa. As a result, there has always been a great need for an effective and economical means to protect, for extended periods of time, both exterior and interior surfaces, various types of substrates and commercial compositions and formulations from the deterioration and destruction caused by such microorganisms.

Materials which need protection with a suitable antimicrobial composition for controlling microorganisms and their adverse effects include, for example, biodegradable compositions including such materials as paints and other coating formulations, surfactants, proteins, starch-based compositions, inks, emulsions and resins, stucco, concrete, stone, and cementaceous surfaces, wood, caulking, sealants, leather, plastics, and textiles as well as materials and other substances which may be attacked by destructive microbes, especially fungi and/or algae. Polymer dispersions or aqueous latex paints containing polyvinyl alcohol, polyacrylates or vinylpolymers, thickener solutions containing cellulose derivatives, kaolin suspensions and metal working fluids, also are prone to degradation by the action of objectionable microorganisms, which can significantly impair the usefulness of such compositions. Such degradation produces changes in pH values, causes gas formation and discoloration and the formation of objectionable odors, and may produce changes in rheological properties.

Wooden objects, in particular, are subject to degradation from a wide variety of natural pests. Fungi are particularly prevalent and include brown rots, white rots and soft rots. Fortunately, a variety of compositions have been developed for treating wooden objects and other materials and surfaces to retard the destructive effect of such pests.

An enormously wide variety of materials have been identified which, to various degrees, are effective in retarding or preventing the growth of, and accompanying destruction caused by, such microbes in such circumstances. Such biocidal compounds include halogenated compounds, organometallic compounds, quaternary ammonium compounds, phenolics, metallic salts, heterocyclic amines, formaldehyde donors, organosulfur compounds and the like.

One well-known class of biocides used in such coating compositions are those containing a halopropynyl moiety, and especially an iodopropynyl moiety. Such compounds are widely disclosed in the patent literature including U.S. Pat. Nos. 3,660,499; 3,923,870; 4,259,350; 4,592,773; 4,616,004 and 4,639,460 to name a few. Included within this class of compounds are the halopropynyl carbamates which are known primarily for their fungicidal activity. 3-iodo-2-propynyl butyl carbamate, hereinafter also referred to as IPBC, is one of the best known and probably the most widely used of the halopropynyl carbamate fungicides. IPBC is a highly active broad spectrum fungicide. In addition to its fungicidal activity, IPBC also has been associated with algaecidal activity. In this regard, Great Britain Patent 2,138,292 and U.S. Pat. Nos. 4,915,909 and 5,082,722 contain such disclosures.

One of the most common ways to apply such materials to surfaces, including wooden objects, to prevent microbial attack is to include them in a composition used to coat the object. The coating, in the form of paints, lacquers and varnishes, functions as a vehicle for the biocidal agent and acts as a barrier to the natural elements, such as sunlight and precipitation. One widely used coating formulation contains an alkyd resin, an oil, an optional solvent thinner and a drier. Another is based on a latex resin emulsion in an aqueous vehicle. Such compositions form dried film coatings by a combination of solvent evaporation, resin oxidation and polymerization.

Haloalkynyl compounds, including halopropynyl compounds, and especially the halopropynyl carbamates, are formulated with a variety of other ingredients in both aqueous and organic solvent mixtures to form such coating materials. For various reasons, it is desired that these coating compositions maintain their biocidal activity for prolonged periods of time.

Unfortunately, this class of biocides is prone to degradation by a variety of mechanisms. One recognized degradation pathway involves ultraviolet (UV) radiation and is primarily a problem in dried coatings containing such biocides. Halopropynyl compounds, and particularly IPBC, are subject to photo-oxidation reactions when exposed to light and are likely to decompose when exposed to sunlight. Organic iodine compounds, in particular, form elemental iodine and other free radical fragments that appear yellow to brown in color. As a result, exposure of surfaces, including dried paint films, containing such compounds, to light causes discoloration and yellowing. This discoloration is especially objectionable in compositions where a white color is desired such as in white caulks, white paints, paper coatings, plastic coatings and the like. Not surprisingly, the prior art has proposed ways of combating the light induced degradation of these halopropynyl compounds.

Gabriele et al., in U.S. Pat. No. 4,552,885 and in Gabriel et al., *Journal of Coatings Technology*, 56(712):33–48, disclose using a 2,2,6,6-tetraalkylpiperidine compound and/or a UV absorber as a way of stabilizing organic fungicidal formulations against light-induced (and particularly ultraviolet light induced) degradation. Such formulations include paints, substrate treatments and protective coatings. IPBC is included in the list of fungicides identified in the patent and is illustrated in the examples.

Singer U.S. Pat. No. 4,276,211 describes adding an organic epoxide stabilizer to compositions containing iodoalkyne carbamates, such as IPBC, to reduce discoloration. Long, U.S. Pat. No. 4,297,258 also recommends using epoxides to reduce the tendency of such fungicides to yellow.

Notwithstanding these prior attempts to reduce the tendency of compositions containing a halopropynyl compound, and particularly a halopropynyl carbamate fungicide such as IPBC, to discolor upon exposure to light, particularly sunlight, and/or heat, the art continues to look for alternative solutions to the discoloration problem.

The present invention provides an improved way to stabilize halopropynyl compounds, and particularly a halopropynyl carbamate fungicide such as IPBC (known in commerce as Troysan Polyphase®), not only in a dry film coating, but also in a wet formulation such as a latex paint, against light and/or heat induced degradation and discoloration.

BRIEF DESCRIPTION OF THE INVENTION

The present invention is based on a discovery of a surprising synergistic effect obtained from a combination of a UV absorber and an organic epoxide on the stabilization of halopropynyl compounds, particularly a halopropynyl carbamate fungicide and compositions containing such compounds, against light-induced and/or heat-induced degradation and discoloration.

In accordance with the invention, it has been discovered that a combination of a UV absorber and an organic epoxide performs synergistically in stabilizing halopropynyl compounds, particularly halopropynyl carbamate fungicides such as the fungicide, 3-iodo-2-propynyl butyl carbamate (IPBC), against color development from degradation induced by light and/or heat.

Relative proportions of the UV absorber and epoxide components in compositions according to the present invention for obtaining such stabilization may be varied widely.

DETAILED DESCRIPTION OF THE INVENTION

The present invention is directed to a synergistically effective combination of a UV absorber and an organic epoxide for stabilizing halopropynyl compounds, particularly halopropynyl carbamate fungicides such as the fungicide, 3-iodo-2-propynyl butyl carbamate.

Halopropynyl compounds stabilized in accordance with the present invention are well known and can be generally identified by the following structure:

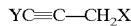

wherein Y is a halogen, preferably iodine and X can be (1) oxygen which is part of an organic functional group; (2) nitrogen which is part of an organic functional group; (3) sulfur which is part of an organic functional group; or (4) carbon which is part of an organic functional group.

The functional group of which oxygen is a part is preferably an ether, an ester, or a carbamate group. The functional group of which nitrogen is a part is preferably an amine, an amide, or a carbamate group. The functional group of which sulfur is a part is preferably a thiol, a thiane, a sulfone, or a sulfoxide group. The organic functional group of which carbon is a part is preferably an ester, a carbamate or an alkyl group.

Examples of compounds which may be used as the halopropynyl compound fungicide of this invention are especially the fungicidally active iodopropynyl derivatives. In this regard, please see U.S. Pat. Nos. 3,923,870, 4,259,350, 4,592,773, 4,616,004, 4,719,227, and 4,945,109, the disclosures of which are herein incorporated by reference. These iodopropynyl derivatives include compounds derived from propynyl or iodopropynyl alcohols such as the esters, ethers, acetals, carbamates and carbonates and the iodopropynyl derivatives of pyrimidines, thiazolinones, tetrazoles, triazinones, sulfamides, benzothiazoles, ammonium salts, carboxamides, hydroxamates, and ureas. Preferred among these compounds is the halopropynyl carbamate, 3-iodo-2-propynyl butyl carbamate. This compound is included within the useful class of compounds having the generic formula:

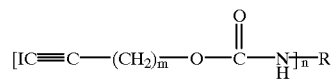

Wherein R is selected from the group consisting of hydrogen, substituted and unsubstituted alkyl groups having from 1 to 20 carbon atoms, substituted and unsubstituted aryl, alkylaryl, and aralkyl or from 6 to 20 carbon atoms or cycloalkyl and cycloalkenyl groups of 3 to 10 carbon atoms, and m and n are independently integers from 1 to 3, i.e., they are not necessarily the same.

Suitable R substituents include alkyls such as methyl, ethyl, propyl, n-butyl, t-butyl, pentyl, hexyl, heptyl, octyl, nonyl, decyl, dodecyl, and octadecyl; cycloalkyls such as cyclohexyl; aryls, alkaryls and aralkyls such as phenyl, benzyl, tolyl, and cumyl; halogenated alkyls and aryls, such as chlorobutryl and chlorophenyl; and alkoxy aryls such as ethoxyphenyl and the like.

Especially preferred are such iodopropynyl carbamates as 3-iodo-2-propynyl propyl carbamate, 3-iodo-2-propynyl butyl carbamate, 3-iodo-2-propynyl hexyl carbamate, 3-iodo-2-propynyl cyclohexyl carbamates, 3-iodo-2-propynyl phenyl carbamate, and mixtures thereof.

UV absorbers used as one of the stabilization-enhancing additives in accordance with the present invention also are well known. In this regard, U.S. Pat. Nos. 3,987,074; 4,129,521; 4,219,480; 4,675,352; 4,760,148; 4,921,966; 5,516,914; 5,436,349; 5,585,091; 3,879,470; 5,281,645; 5,342,610; 5,468,904; 5,601,756; 5,047,571; 4,654,434; 4,710,584; and 5,144,081 (the disclosures of which are incorporated herein by reference) describe a wide variety of suitable additiives that potentially can be used in the present invention. Preferably, a UV absorber for use in the invention is selected from one of the following three major classes of known UV absorbers: (1) benzotriazoles, (2) benzophenones and (3) substituted ethenes.

A first class of UV absorbers useful in the invention are the benzotriazoles. Benzotriazole UV absorbers are widely described in the prior art. In this regard, please refer to the following U.S. Pat. Nos. 3,987,074; 4,129,521; 4,219,480; 4,675,352; 4,760,148; 4,921,966; 5,516,914; 5,436,349 and 5,585,091 as representative examples. A suitable, though not exclusive, class of benzotriazole UV absorbers include compounds represented by the following formula with $R^1$, $R^2$, $R^3$, $R^4$ and $R^5$ generally selected from such substituents as hydrogen; halogen (e.g., chlorine); an alkyl group; an is aryl group; an aralkyl; an alkoxy group; an alkanoyl group; a carboxy group; —$SO_3H$; a hydroxy; a cycloalkyl group; an alkyl group substituted with hydroxy, alkoxy, or an amino; or an aryl or aralkyl group substituted with alkyl group(s):

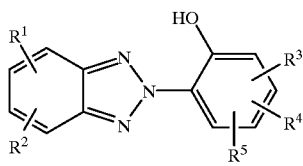

A variety of benzotriazole UV absorbers are commercially available. Representative products include Tinuvin 328, Tinuvin 9000, Tinuvin 1130, Tinuvin 384, Tinuvin 109, Tinuvin P (all from Ciba-Geigy), Uvasorb SV (SV Inc.) and Cyasorb (Cytec).

A second class of UV absorbers useful in the invention are the benzophenones. Benzophenones UV absorbers also are widely described in the prior art. In this regard, please refer to the following U.S. Pat. Nos. 3,879,470; 5,281,645; 5,342,610; 5,468,904 and 5,601,756 as representative examples. A suitable, though not exclusive, class of benzophenone UV absorbers include compounds represented by the following formula with $R^1$, $R^2$, $R^3$, $R^4$, $R^5$ and $R^6$ generally selected from such substituents as hydrogen, halogen (e.g., chlorine); an alkyl group; an aryl group; an aralkyl; a carboxy group; an alkoxy group optionally substituted with a carboxy group; an alkenyl group; an alkenyloxy group; an alkanoyl group; a hydroxy; a cycloalkyl group; —$SO_3H$; an alkyl group substituted with hydroxy or alkoxy; an aryl or an aralkyl group substituted with alkyl group(s), or one or more substituted benzophenone groups:

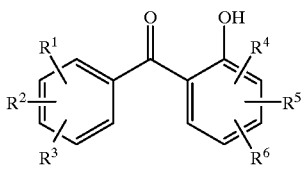

Table A illustrates a number of bezophenones suitable for use in the present invention.

TABLE A

| Entry | $R^1$ | $R^2$ | $R^3$ |
|---|---|---|---|
| 1 | H— | H— | HO— |
| 2 | H— | H— | $H_3CO$— |
| 3 | H— | H— | $H_{17}C_8O$— |
| 4 | H— | H— | $H_2C$=$HCH_2CO$— |
| 5 | HO— | $H_3CO$— | $H_3CO$— |
| 6 | HO— | HO— | HO— |
| 7 | HO— | H— | H— |
| 8 | HO— | H— | $H_3CO$— |
| 9 | HO— | H— | (acrylate ester group) |

Such benzophenones also include 2-hydroxy4-methoxybenzophenone; 2,4-dihydroxybenzophenone; 2-hydroxy4-methoxybenzophenone-5-sulfonic acid; sodium 2,2'-dihydroxy-4,4'-dimethoxy-5-sulfo-benzophenone; 2-hydroxy4-n-octoxybenzophenone; 2-hydroxy-4-methoxybenzophenone and 2,2'-dihydroxy-4-methoxybenzophenone.

The third class of UV absorbers particularly useful in the invention are the substituted ethenes, especially the acrylate and benzylidene-camphore type substituted ethene UV absorbers. Substituted ethene UV absorbers also are widely described in the prior art. In this regard, please refer to the following U.S. Pat. Nos. 5,047,571; 4,654,434; 4,710,584; and 5,144,081 as representative examples. A suitable, though not exclusive, class of substituted ethene UV absorbers include the acrylate type compounds represented by the following formula with $R^1$, $R^2$, $R^3$, and $R^4$ generally selected from such substituents as hydrogen; an alkyl group optionally substituted with an aryl group optionally substituted with an alkyl group, an alkoxy group, a halogen (preferably chlorine), and aryl group and an cyano group (—C≡N); wherein at least one of the substituents ia an alkoxy carbonyl group.

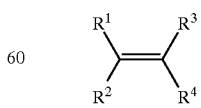

Table B illustrates a number of substituted ethenes suitable for use in connection with the present invention.

TABLE B

| Entry | R¹ | R² | R³ | R⁴ |
|---|---|---|---|---|
| 1 | phenyl | H— | ethyl acetate group | N≡C— |
| 2 | phenyl | H— | ethyl acetate group | ethyl acetate group |
| 3 | phenyl | H— | 2-ethylhexyl acetate group | N≡C— |
| 4 | phenyl | phenyl | ethyl acetate group | N≡C— |
| 5 | phenyl | phenyl | 2-ethylhexyl acetate group | N≡C— |
| 6 | H₃CO-phenyl | H— | ethyl acetate group | ethyl acetate group |
| 7 | H₃CO-phenyl | H— | 2-ethylhexyl acetate group | H— |
| 8 | H₃CO-phenyl | H— | ethyl acetate group | N≡C— |
| 9 | H₃CO-phenyl | H— | methyl acetate group | methyl acetate group |

Also included within the class of substituted ethene UV absorbers are the benzylidene-camphors such as 3-(4-methylbenzyidene)-camphor; 3-(2',5'-dimethoxybenzylidene)camphor; 3-(2',5'-diethoxybenzylidene)camphor; 3-(2',5'-dipropxybenzylidene)camphor; 3-(2',5'-dimethoxybenzylidene)camphor-10-sulfonic acid; 3-(2',5'-diethoxybenzylidene)camphor-10-sulfonic acid; and 3-(2', 5'-dipropoxybenzylidene)camphor-10-sulfonic acid.

The other additive which acts synergistically with the UV absorber in stabilizing compositions containing a halopropynyl compound is an organic epoxide. Epoxides useful in practicing the present invention also are well known materials and have one or more of the following radicals in their structure:

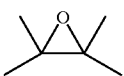

Such epoxides include those of the following general structural formula:

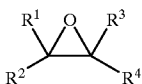

with $R^1$, $R^2$, $R^3$ and $R^4$ independently selected from a wide variety of radicals including hydrogen; an alkyl group of 1 to 20 carbon atoms such as methyl, ethyl, propyl, butyl, pentyl and the like; a substituted alkyl group; a halogen; a hydroxy; an aryl group; a substituted aryl group; an alkoxy group; an alkoxyalkyl group such as methoxymethyl, ethoxymethyl, propoxyethyl, n-butoxyethyl, tert-butoxymethyl, tert butoxybutyl and the like; a 2,3-epoxy di-alkoxy alkyl group, such as 2,3-epoxy-1-propoxy-ethoxymethyl, 2,3-epoxy-1-butoxyethoxyethyl and the like; an aryl group; an aralkyl group; an aryloxy group; an aryloxyalkyl group; or an alkanoyl group; $R^1$, $R^2$, $R^3$ or $R^4$ may also be a radical of the formula:

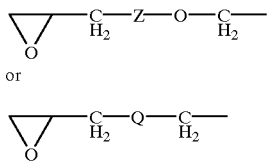

wherein Z is a straight or branched chain lower alkylene, for example propylene, butylene, pentylene, hexylene, heptylene and the like; or a halo substituted lower alkylene such as 2,2-dibromomethyl propylene, 2,2-dichloromethyl propylene and the like; and Q is $(C_1-C_4)$alkylene or carbonylarylcarboxy such as carbonylphenylcarboxy and the like; or one of $R^1$ or $R^2$ and one of $R^3$ or $R^4$ are joined together with the carbon to which they are attached, to form an alkylene chain of from 3 to 7 carbon atoms, which alkylene chain may be substituted with a lower alkylene to form a bicyclo alkane for example, bicyclo[3.1.1] heptane, bicyclo[2.2.2.]octane and the like, or substituted with a lower alkenyl radical such as ethenyl, 1-methylethenyl, butenyl and the like; all of these groups may further be optionally substituted with one or more additional epoxide groups.

Suitable epoxy compounds are those wherein $R^1$ is hydrogen, lower alkoxy, lower alkyl, or 2,3-epoxy-1-propoxyethoxymethyl, $R^2$ is hydrogen or lower alkyl, $R^3$ and $R^4$ are hydrogen, or $R^1$ or $R^2$ and one of $R^3$ or $R^4$ may be joined together with the carbon atom to which they are attached to form an alkylene chain of from 3 to 7 carbon atoms, which alkylene chain may be substituted with a lower alkylene to form a bicycloalkane.

Representative examples of suitable epoxides for use in the present invention include:

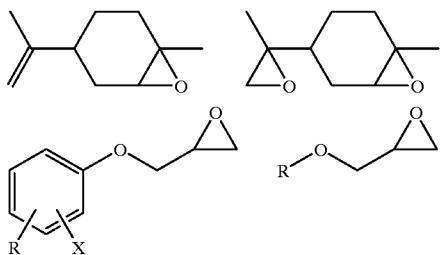

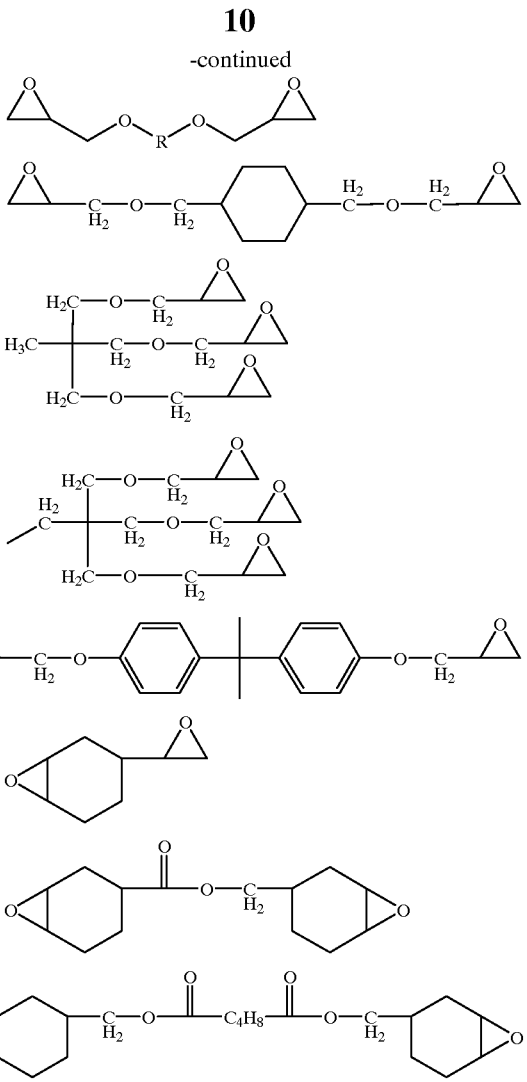

The term "alkyl", when used alone or in combination, means a straight-chain or branched-chain alkyl radical containing from 1 to about 20, preferably from 1 to about 12, carbon atoms. Examples of such radicals include methyl, ethyl, n-propyl, isopropyl, n-butyl, isobutyl, sec-butyl, tert-butyl, pentyl, iso-amyl, hexyl, octyl and the like. Alkyls often may be optionally substituted by an alkoxy (preferably a lower alkoxy), nitro, monoalkylamino (preferably a lower alkylamino), dialkylamino (preferably a di[lower] alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. The term "alkenyl", alone or in combination, means a straight-chain or branched-chain hydrocarbon radial having one or more double bonds and containing from 2 to about 18 carbon atoms preferably from 2 to about 8 carbon atoms. Examples of suitable alkenyl radicals include ethenyl, propynyl, allyl, 1,4-butadienyl and the like. The term "alkoxy" as used alone or in combination herein refers to a straight or branched chain alkyl group covalently bonded to the parent molecule through an —O— linkage, i.e., an alkyl ether radical wherein the term alkyl is as defined above. Examples of suitable alkoxy radicals include methoxy, ethoxy, propoxy, isopropoxy, butoxy, n-butoxy, sec-butoxy, t-butoxy and the like. The term "alkenyloxy" refers to a straight-chain or branched-chain hydrocarbon radial having one or more double bonds covalently bonded to the parent molecule through an —O— linkage, i.e., an alkenyl ether radical wherein the term alkenyl is as defined above. The term "aryl", alone or in combination, means a carbocyclic aromatic system containing one, two or three rings wherein such rings may be attached together in a pendent manner or may be fused. Examples of "aryl" include phenyl or naphthyl radical either of which optionally carries one or more substituents selected from alkyl, alkoxy, halogen, hydroxy, amino and the like, such as p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. Phenyl is generally preferred. The term "aralkyl", alone or in combination, means an alkyl radical as defined above in which one hydrogen atom is replaced by an aryl radical as defined above, such as benzyl, 2-phenylethyl and the like. Examples of substituted aralkyl include 3,5-dimethoxybenzyl, 3,4-dimethoxybenzyl, 2,4-dimethoxybenzyl, 3,4,5-trimethoxy-benzyl, 2,6-dichlorobenzyl, and 1,4-bis(chloromethyl)benzene. The term "halogen" means fluorine, chlorine, bromine or iodine,; chlorine generally is preferred. The term "alkanoyl", alone or in combination, means an acyl radical derived from an alkanecarboxylic acid wherein alkane means a radical as defined above for alkyl. Examples of alkanoyl radicals include acetyl, propionyl, butyryl, valeryl, 4-methylvaleryl, and the like. The term "alkoxy carbonyl," alone or in combination, means a radical of the formula —C(O)—O-alkyl in which the term "alkyl" has the significance given above. The term "aralkoxy carbonyl", alone or in combination, means a radical of the formula —C(O)—O-aralkyl in which the term "aralkyl" has the significance given above. An example of an aralkoxycarbonyl radical is benzyloxycarbonyl. The term "carboxy" means a radical of the formula R—C(O)O— where R may be an alkyl or alkenyl group.

The combination of UV absorber and epoxide components finds its primary utility in stabilizing halopropynyl compounds, particularly halopropynyl carbamate fungicides such as the fungicide, 3-iodo-2-propynyl butyl carbamate (IPBC), in lattices such as acrylic lattices, vinyl acetate acrylic lattices, polyvinyl acetate lattices, styrene butadiene lattices, in silicone formulations used for paints and caulks, as well as in leather treatment fluids, other wood treatment fluids and metal working fluids.

Relative proportions of the UV absorber and epoxide components in the composition can vary widely and the synergistic behavior of a particular proportion may be affected by the intended application and the particular compounds selected. In this regard, certain combinations of a UV absorber and an organic epoxide have exhibited greater or lesser degrees of synergistic behavior which performance is easily gauged by routine testing as described in the following examples. In any event, it is expected that compositions containing a little as 1 part of a UV absorber to 9 parts of an organic epoxide and conversely as little as 1 part of an organic epoxide to 9 parts of a UV absorber will be useful. Typically, useful compositions will contain from 4:1 to 1:4 parts of the UV absorber to the organic epoxide and more usually from 3:1 to 1:2 relative parts by weight.

In accordance with the invention, the halopropynyl compound can be included in a final formulation for use in such end use applications as paints, coatings, stucco, plastics, concrete, stone, cementaceous surfaces, wood, caulking, sealants, textiles, and the like, in a broad range from about 0.004% to 5.0% active concentration, more usually in a range from about 0.01% to 2%. Such compositions can be prepared from highly concentrated compositions of the active ingredients by appropriate dilution. The optimum useful range is normally about 0.1% to 0.3% of halopropynyl compound in the final formulations for such end use systems. With the use of such formulations in end use systems, it is possible to protect surfaces as well as other substrates for extended periods of time against microbial growth.

The combination of the UV absorber and epoxide components will normally be added in an amount of from about 10% to 400% by weight of the halopropynyl compound, and more usually from 10% to 300% by weight.

Compositions of the present invention will generally be formulated by mixing the combination of the UV absorber and epoxide components in a selected proportion relative to the halopropynyl compound in a liquid vehicle for dissolving or suspending the active components. The present invention specifically contemplates the preparation of a concentrate containing a liquid vehicle and the above three noted constituents. The concentrate is useful for adding a halopropanyl compound into particular formulations in the form of a stabilized biocide. The vehicle also may contain a diluent, an emulsifier and a wetting-agent. As noted above, expected uses of the biocidal compositions include protection of wood, paint, coatings, adhesives, paper, textiles, plastics, cardboard, lubricants, caulkings, and the like. An extensive list of potential industries and applications for the present invention can be found in U.S. Pat. No. 5,209,930 which is herein incorporated by reference.

Useful liquid vehicles for the halopropynyl compound, particularly the preferred iodopropynyl butyl carbamate are several glycol ethers and esters like propylene glycol n-butyl ether, propylene glycol tert-butyl ether, 2(2-methoxymethylethoxy)-tripropylene glycol methyl ether, propylene glycol methyl ether, dipropyleneglycol methyl ether, tripropylenelene glycol methyl ether, propylene glycol n-butyl ether and the esters of the previously mentioned compounds. Other useful solvents are n-methyl pyrrolidone, n-pentyl propionate and dibasic esters of several dicarboxylic acids and mixes thereof In many applications, a preferred liquid vehicle for these products can be selected from n-methyl pyrrolidone, propylene glycol n-butyl ether, 1-methoxy-2-propanol, and the dibasic isobutyl ester blend of succinic, glutaric and adipic acids.

When preparing formulations of the present invention for specific applications, the composition also will likely be provided with other adjuvants conventionally employed in compositions intended for such applications such as organic binding agents, additional fungicides, auxiliary solvents, processing additives, fixatives, plasticizers, water soluble or water insoluble dyes, color pigments, siccatives, corrosion inhibitors, antisettlement agents, anti-skinning agents and the like. Additional fungicides used in the composition are preferably soluble in the liquid vehicle.

According to the present invention, substrates are protected from infestation by fungal organisms simply by treating said substrate with a composition of the present invention. Such treating may involve mixing the composition with the substrate, coating or otherwise contacting the substrate with the composition and the like.

As noted, the present invention is directed to synergistically stabilized compositions containing a halopropynyl compound, stabilized in a synergistic manner by a combination of at least one UV absorber and at least one organic epoxide component. A synergistic effect is generally regarded as the response of a mixture of two or more components that is greater than the sum of the response of the individual components. In a general sense, a mathematical approach for assessing synergy, as reported by F. C. Kull, P. C. Elisman, H. D. Sylwestrowicz and P. K. Mayer, in *Applied Microbiology*, 9:538 (1961) can be applied to binary mixtures using the following equation:

$$\text{Synergistic Index (SI)} = Q_a/Q_A + Q_b Q_B$$

where:

$Q_a$=the quantity of component A used in a ternary mixture that gives the desired effect (such as no reduced biocide degradation), $Q_A$=the quantity of component A which when used alone gives the desired effect, $Q_b$=the quantity of component B used in a ternary mixture that gives the desired effect, and $Q_B$=the quantity of component B which when used alone gives the desired effect.

If the SI for a composition is less than one (<1), that composition exhibits synergistic behavior.

The following examples are presented to illustrate and explain the invention. Unless otherwise indicated, all references to parts and percentages are based on weight.

EXAMPLES

In the following examples a styrenated white house paint was used as the test medium to measure the effect of sunlight on the degradation of IPBC in various IPBC-containing compositions. The composition of the paint is shown in Table 1. The test paint composition was prepared by adding ingredients 2 through 6 slowly to a mixer containing water (ingredient 1). After mixing the composition for about 10 minutes, ingredients 7 through 11 were added, and mixing was continued until a smooth dispersion was obtained. Then the final two ingredients were added. Additional water can be added to obtain a desired viscosity.

TABLE 1

| No. | Ingredient | Supplier | % W/W |
|---|---|---|---|
|  | Raw Materials | Suppliers | % |
| 1 | Water |  | 9.30 |
| 2 | Tamol 850 (30%) | Rohm & Haas | 0.20 |
| 3 | Triton CF-10 | Union Carbide | 0.50 |
| 4 | KTPP | FMC | 0.50 |
| 5 | NH₄OH (7.0%) |  | 0.20 |
| 6 | Collateral P: Water (1:1) | BASF | 3.00 |
| 7 | Mineral Spirits |  | 1.20 |
| 8 | Texanol | Eastman Chemicals | 0.80 |
| 9 | TiO₂ | Kerr-McGee | 15.00 |
| 10 | Camel White (CaCO₃) | Genstar | 26.00 |
| 11 | Nytal 300 | R.T. Vanderbilt | 6.40 |
| 12 | Nopco 8035 | Huls | 0.30 |
| 13 | Acronal 296D | BASF | 36.60 |
|  | TOTAL |  | 100.00 |

In the following examples, a number of liquid formulations containing (1) 20% by weight Troysan Polyphase® P100 (IPBC), (2) a UV absorber and/or an organic epoxide, in an amount as indicated for the appropriate entry in each of the tables which follow, and (3) the balance (up to 100% by weight) of N-methyl pyrrolidone as a liquid vehicle, were prepared and were then incorporated into the white test paint by mixing to provide 0.3% IPBC in the test paint. The paint formulations containing IPBC and the candidate compound (s) (mixtures) then were applied on a Leneta chart with help of a 3 mil Bird type applicator. The paint film was allowed to dry for 10–15 minutes and then sprayed with a clear non-yellowing varnish (~3 mils), namely, Kamar Varnish 1312. The varnish was obtained from Krylon Products Group, The Specialty Division, Division of Sherwin-Williams Company, Ohio. The object of the varnish was to trap all the chromophores produced during subsequent light exposure and to obtain a short and reproducible test for accessing light-induced yellowing. The paint film thus produced was exposed to 340 nm UV radiation for four hours and the yellowing was measured by Microflash 200D or Byk Handy Color measurement device. The difference in yellowing between a blank (the white test paint without fungicide) and the candidate paint sample, Δb, was recorded and used as the response for each test. A paint formulation, which did not contain any UV absorber or epoxide additive but which did have the same amount of IPBC as all the other IPBC-containing paint formulations, also was tested and served as the control response.

The following tables report the results obtained using several different UV absorber and epoxide additives. The data point reported for each entry of the following tables is a ratio of the Δb for the control formulation (paint with IPBC without any UV absorber or epoxide additive) to the Δb for the formulation containing the UV absorber and/or the epoxide. An expected Δb ratio also was calculated (and is similarly reported in the tables) for the various combinations of additives based on the experimental response obtained for the highest level of components A and B used alone. The expected Δb was calculated in accordance with the following formula:

$R_c = (Q_a/Q_A) \cdot R_A + (Q_b/Q_B) \cdot R_B$

Where
- $R_c$ is the expected (calculated) Δb ratio;
- $R_A$ is the Δb ratio obtained at the maximum concentration of UV absorber (component A) used alone;
- $R_B$ is the Δb ratio obtained at the maximum concentration of epoxide additive (component B) used alone;
- $Q_a/Q_A$ is the ratio of the weight percent of UV absorber in the tested formulation to the weight percent of UV absorber in the maximum concentration tested; and
- $Q_b/Q_B$ is the ratio of the weight percent of epoxide additive in the tested formulation to the weight percent of epoxide additive in the maximum concentration tested.

If the experimentally measured Δb ratio was greater than the expected response ($R_c$) calculated for the tested combination, then the composition can be considered to be synergistic.

Example 1

This example reports the results of using a mixture of 3-(4-methylbenzylidene) camphor as the UV absorber (component A) and the diglycidyl ether of 1,4-butanediol as the organic epoxide (component B).

TABLE 2

| $Q_a$ | $Q_b$ | Δb Ratio (Experimental) | Δb Ratio (Calculated) | Synergy |
|---|---|---|---|---|
| 40 | — | 3.55 | | |
| 20 | 5 | 3.08 | 2.18 | yes |
| 20 | 10 | 3.71 | 2.58 | yes |
| 15 | 15 | 3.45 | 2.54 | yes |
| 15 | 20 | 16.38 | 2.94 | yes |
| 10 | 10 | 5.86 | 1.69 | yes |
| 10 | 20 | 5.33 | 2.50 | yes |
| — | 40 | 3.22 | | |

Example 2

This example reports the results of using a mixture of 3-(4-methylbenzylidene) camphor as the UV absorber (component A) and cresyl glycidyl ether as the organic epoxide (component B).

TABLE 3

| $Q_a$ | $Q_b$ | Δb Ratio (Experimental) | Δb Ratio (Calculated) | Synergy |
|---|---|---|---|---|
| 40 | — | 3.55 | | |
| 20 | 5 | 2.68 | 2.12 | yes |
| 20 | 10 | 3.11 | 2.47 | yes |
| 15 | 15 | 3.29 | 2.37 | yes |
| 15 | 20 | 4.16 | 2.72 | yes |
| 10 | 10 | 3.04 | 1.58 | yes |
| 10 | 20 | 2.9 | 2.28 | yes |
| — | 40 | 2.78 | | |

Example 3

This example reports the results of using a mixture of 3-(4-methylbenzylidene) camphor as the UV absorber (component A) and the Trimethylol propane trigylcidyl ether as the organic epoxide (component B).

TABLE 4

| $Q_a$ | $Q_b$ | Δb Ratio (Experimental) | Δb Ratio (Calculated) | Synergy |
|---|---|---|---|---|
| 40 | — | 3.55 | | |
| 20 | 5 | 2.84 | 2.12 | yes |
| 20 | 10 | 4.12 | 2.46 | yes |
| 15 | 15 | 3.7 | 2.36 | yes |
| 15 | 20 | 5.92 | 2.71 | yes |
| 10 | 10 | 2.26 | 1.58 | yes |
| 10 | 20 | 4.01 | 2.26 | yes |
| — | 40 | 2.75 | | |

Example 4

This example reports the results of using a mixture of 3-(4-methylbenzylidene) camphor as the UV absorber (component A) and Araldite GY506 (supplied by Ciba-Geigy) as the organic epoxide (component B).

TABLE 5

| $Q_a$ | $Q_b$ | Δb Ratio (Experimental) | Δb Ratio (Calculated) | Synergy |
|---|---|---|---|---|
| 40 | — | 3.55 | | |
| 20 | 5 | 2.64 | 2.08 | yes |
| 20 | 10 | 3.3 | 2.39 | yes |
| 15 | 15 | 3 | 2.25 | yes |
| 15 | 20 | 3.18 | 2.56 | yes |
| 10 | 10 | 3.24 | 1.5 | yes |
| 10 | 20 | 6.12 | 2.11 | yes |
| — | 40 | 2.45 | | |

Example 5

This example reports the results of using a mixture of 3-(4-methylbenzylidene) camphor as the UV absorber (component A) and the Aliphatic $C_{12}$–$C_{14}$ glycidyl ether (Araldite DY 025, supplied by Ciba-Geigy) as the organic epoxide (component B).

TABLE 6

| $Q_a$ | $Q_b$ | Δb Ratio (Experimental) | Δb Ratio (Calculated) | Synergy |
|---|---|---|---|---|
| 40 | — | 3.55 | | |
| 20 | 5 | 3.51 | 2.11 | yes |
| 20 | 10 | 3.25 | 2.45 | yes |
| 15 | 15 | 2.65 | 2.34 | yes |
| 15 | 20 | 3.7 | 2.68 | yes |
| 10 | 10 | 2.56 | 1.56 | yes |
| 10 | 20 | 2.89 | 2.23 | yes |
| — | 40 | 2.69 | | |

Example 6

This example reports the results of using a mixture of Octyl methoxycinnamate (A) as the UV absorber (component A) and the diglycidyl ether of 1,4-butanediol as the organic epoxide (component B).

TABLE 7

| $Q_a$ | $Q_b$ | Δb Ratio (Experimental) | Δb Ratio (Calculated) | Synergy |
|---|---|---|---|---|
| 40 | — | 2.31 | | |
| 20 | 5 | 2.78 | 1.56 | yes |
| 20 | 10 | 4.85 | 1.96 | yes |
| 15 | 15 | 2.4 | 2.07 | yes |
| 15 | 20 | 3.21 | 2.48 | yes |
| 10 | 10 | 3.66 | 1.38 | yes |
| 10 | 20 | 6.46 | 2.19 | yes |
| | 40 | 3.22 | | |

Example 7

This example reports the results of using a mixture of Octyl methoxycinnamate (A) as the UV absorber (component A) and Cresyl glycidyl ether as the organic epoxide (component B).

TABLE 8

| $Q_a$ | $Q_b$ | Δb Ratio (Experimental) | Δb Ratio (Calculated) | Synergy |
|---|---|---|---|---|
| 40 | — | 2.31 | | |
| 20 | 5 | 1.71 | 1.50 | yes |
| 20 | 10 | 1.74 | 1.85 | no |
| 15 | 15 | 2.2 | 1.91 | yes |
| 15 | 20 | 2.69 | 2.26 | yes |
| 10 | 10 | 2.05 | 1.27 | yes |
| 10 | 20 | 2.26 | 1.97 | yes |
| | 40 | 2.78 | | |

Example 8

The example reports the results of using a mixture of Octyl methoxycinnamate (A) as the UV absorber (component A) and trimethylol propane trigylcidyl ether as the organic epoxide (component B).

TABLE 9

| $Q_a$ | $Q_b$ | Δb Ratio (Experimental) | Δb Ratio (Calculated) | Synergy |
|---|---|---|---|---|
| 40 | — | 2.31 | | |
| 20 | 5 | 1.83 | 1.50 | yes |
| 20 | 10 | 1.97 | 1.84 | yes |
| 15 | 15 | 3.1 | 1.90 | yes |
| 15 | 20 | 2.08 | 2.24 | no |
| 10 | 10 | 1.61 | 1.26 | yes |
| 10 | 20 | 1.8 | 1.95 | no |
| | 40 | 2.75 | | |

Example 9

This example reports the results of using a mixture of Octyl methoxycinnamate (A) as the UV absorber (component A) and Araldite GY506 (supplied by Ciba-Geigy) as the organic epoxide (component B).

TABLE 10

| $Q_a$ | $Q_b$ | Δb Ratio (Experimental) | Δb Ratio (Calculated) | Synergy |
|---|---|---|---|---|
| 40 | — | 2.31 | | |
| 20 | 5 | 2.4 | 1.46 | yes |
| 20 | 10 | 2.34 | 1.77 | yes |
| 15 | 15 | 2.54 | 1.78 | yes |
| 15 | 20 | 4.02 | 2.09 | yes |
| 10 | 10 | 2.12 | 1.19 | yes |
| 10 | 20 | 2.08 | 1.80 | yes |
| | 40 | 2.45 | | |

Example 10

This example reports the results of using a mixture of Octyl methoxycinnamate (A) as the UV absorber (component A) and Aliphatic $C_{12}$–$C_{14}$ glycidyl ether (Araldite DY 025, supplied by Ciba-Geigy) as the organic epoxide (component B).

TABLE 11

| $Q_a$ | $Q_b$ | Δb Ratio (Experimental) | Δb Ratio (Calculated) | Synergy |
|---|---|---|---|---|
| 40 | — | 2.31 | | |
| 20 | 5 | 2.54 | 1.49 | yes |
| 20 | 10 | 2.99 | 1.83 | yes |
| 15 | 15 | 2.09 | 1.88 | yes |
| 15 | 20 | 2.86 | 2.21 | yes |
| 10 | 10 | 1.98 | 1.25 | yes |
| 10 | 20 | 2.26 | 1.92 | yes |
| | 40 | 2.69 | | |

Example 11

This example reports the results of using a mixture of ethylhexyl-2-cyano-3,3-diphenylacrylate (A) as the absorber (component A) and the diglycidyl ether of 1,4-butanediol as the organic epoxide (component B).

TABLE 12

| $Q_a$ | $Q_b$ | Δb Ratio (Experimental) | Δb Ratio (Calculated) | Synergy |
|---|---|---|---|---|
| 40 | — | 2.27 | | |
| 20 | 5 | 4.43 | 1.54 | yes |
| 20 | 10 | 3.7 | 1.94 | yes |
| 15 | 15 | 2.49 | 2.06 | yes |
| 15 | 20 | 8.19 | 2.46 | yes |
| 10 | 10 | 3.3 | 1.37 | yes |
| 10 | 20 | 4 | 2.18 | yes |
| | 40 | 3.22 | | |

Example 12

This example reports the results of using a mixture of ethylhexyl-2-cyano-3,3-diphenylacrylate (A) as the UV absorber (component A) and Cresyl glycidyl ether as the organic epoxide (component B).

TABLE 13

| $Q_a$ | $Q_b$ | Δb Ratio (Experimental) | Δb Ratio (Calculated) | Synergy |
|---|---|---|---|---|
| 40 | — | 2.27 | | |
| 20 | 5 | 3.19 | 1.48 | yes |
| 20 | 10 | 2.73 | 1.83 | yes |
| 15 | 15 | 2.47 | 1.89 | yes |
| 15 | 20 | 3.8 | 2.24 | yes |
| 10 | 10 | 2.5 | 1.26 | yes |
| 10 | 20 | 6 | 1.96 | yes |
| | 40 | 2.78 | | |

Example 13

This example reports the results of using a mixture of Ethylhexyl-2-cyano-3,3-diphenaylacrylate (A) as the UV absorber (component A) and trimethylol propane trigylcidyl ether as the organic epoxide (component B).

TABLE 14

| $Q_a$ | $Q_b$ | Δb Ratio (Experimental) | Δb Ratio (Calculated) | Synergy |
|---|---|---|---|---|
| 40 | — | 2.27 | | |
| 20 | 5 | 2.72 | 1.48 | yes |
| 20 | 10 | 3.48 | 1.82 | yes |
| 15 | 15 | 2.5 | 1.88 | yes |
| 15 | 20 | 3.68 | 2.23 | yes |
| 10 | 10 | 1.61 | 1.26 | yes |
| 10 | 20 | 2.73 | 1.94 | yes |
| | 40 | 2.75 | | |

Example 14

This example reports the results of using a mixture of Ethylhexyl-2-cyano-3,3-diphenaylacrylate (A) as the UV absorber (component A) and Araldite GY506 (supplied by Ciba-Geigy) as the organic epoxide (component B).

TABLE 15

| $Q_a$ | $Q_b$ | Δb Ratio (Experimental) | Δb Ratio (Calculated) | Synergy |
|---|---|---|---|---|
| 40 | — | 2.27 | | |
| 20 | 5 | 2.59 | 1.44 | yes |
| 20 | 10 | 3.14 | 1.75 | yes |
| 15 | 15 | 2.65 | 1.77 | yes |
| 15 | 20 | 3.48 | 2.08 | yes |
| 10 | 10 | 2.03 | 1.18 | yes |
| 10 | 20 | 2.61 | 1.79 | yes |
| — | 40 | 2.45 | | |

Example 15

This example reports the results of using a mixture of Ethylhexyl-2-cyano-3,3-diphenaylacrylate (A) as the UV absorber (component A) and Aliphatic $C_{12}$–$C_{14}$ glycidyl ether (Araldite DY 025, supplied by Ciba-Geigy) as the organic epoxide (component B).

TABLE 16

| $Q_a$ | $Q_b$ | Δb Ratio (Experimental) | Δb Ratio (Calculated) | Synergy |
|---|---|---|---|---|
| 40 | — | 2.27 | | |
| 20 | 5 | 4.96 | 1.47 | yes |
| 20 | 10 | 8.31 | 1.81 | yes |
| 15 | 15 | 1.8 | 1.86 | no |
| 15 | 20 | 2.73 | 2.20 | yes |
| 10 | 10 | 2.98 | 1.24 | yes |
| 10 | 20 | 5.95 | 1.91 | yes |
| — | 40 | 2.69 | | |

Example 16

This example reports the results of using a mixture of Tinuvin 1130 (supplied by Ciba-Geigy) as the UV absorber (component A) and the diglycidyl ether of 1,4-butanediol as the organic epoxide (component B).

TABLE 17

| $Q_a$ | $Q_b$ | Δb Ratio (Experimental) | Δb Ratio (Calculated) | Synergy |
|---|---|---|---|---|
| 40 | — | 2.06 | | |
| 20 | 5 | 2.98 | 1.43 | yes |
| 20 | 10 | 4.32 | 1.83 | yes |
| 15 | 15 | 1.63 | 1.98 | no |
| 15 | 20 | 2.24 | 2.38 | no |
| 10 | 10 | 2.54 | 1.32 | yes |
| 10 | 20 | 4.46 | 2.12 | yes |
| — | 40 | 3.22 | | |

Example 17

This example reports the results of using a mixture of Tinuvin 1130 (supplied by Ciba-Geigy) as the UV absorber (component A) and Cresyl glycidyl ether as the organic epoxide (component B).

TABLE 18

| $Q_a$ | $Q_b$ | Δb Ratio (Experimental) | Δb Ratio (Calculated) | Synergy |
|---|---|---|---|---|
| 40 | — | 2.06 | | |
| 20 | 5 | 1.62 | 1.38 | yes |
| 20 | 10 | 1.52 | 1.72 | no |
| 15 | 15 | 1.77 | 1.82 | no |
| 15 | 20 | 1.54 | 2.16 | no |
| 10 | 10 | 1.84 | 1.21 | yes |
| 10 | 20 | 2.06 | 1.90 | yes |
| | 40 | 2.78 | | |

Example 18

This example reports the results of using a mixture of Tinuvin 1 130 (supplied by Ciba-Geigy) as the UV absorber (component A) and trimethylol propane trigylcidyl ether as the organic epoxide (component B).

TABLE 19

| $Q_a$ | $Q_b$ | Δb Ratio (Experimental) | Δb Ratio (Calculated) | Synergy |
|---|---|---|---|---|
| 40 | — | 2.06 | | |
| 20 | 5 | 1.35 | 1.37 | no |
| 20 | 10 | 1.79 | 1.72 | yes |
| 15 | 15 | 1.79 | 1.80 | no |
| 15 | 20 | 1.92 | 2.15 | no |
| 10 | 10 | 1.49 | 1.20 | yes |
| 10 | 20 | 2.02 | 1.89 | yes |
| — | 40 | 2.75 | | |

Example 19

This example reports the results of using a mixture of Tinuvin 1130 (supplied by Ciba-Geigy) as the UV absorber (component A) and Araldite GY506 (supplied by Ciba-Geigy) as the organic epoxide (component B).

TABLE 20

| $Q_a$ | $Q_b$ | Δb Ratio (Experimental) | Δb Ratio (Calculated) | Synergy |
|---|---|---|---|---|
| 40 | — | 2.06 | | |
| 20 | 5 | 1.09 | 1.34 | no |
| 20 | 10 | 1.38 | 1.64 | no |
| 15 | 15 | 1.91 | 1.69 | yes |
| 15 | 20 | 1.44 | 2.00 | no |
| 10 | 10 | 1.48 | 1.13 | yes |
| 10 | 20 | 1.5 | 1.74 | no |
| — | 40 | 2.45 | | |

Example 20

This example reports the results of using a mixture of 2-Hydroxy-4-methoxy-benzophenone as the UV absorber (component A) and the diglycidyl ether of 1,4-butanediol as the organic epoxide (component B).

TABLE 21

| $Q_a$ | $Q_b$ | Δb Ratio (Experimental) | Δb Ratio (Calculated) | Synergy |
|---|---|---|---|---|
| 40 | — | 2.06 | | |
| 20 | 5 | 1.77 | 1.37 | yes |
| 20 | 10 | 1.28 | 1.70 | no |
| 15 | 15 | 1.24 | 1.78 | no |
| 15 | 20 | 1.31 | 2.12 | no |
| 10 | 10 | 1.19 | 1.19 | yes |
| 10 | 20 | 1.09 | 1.86 | no |
| — | 40 | 2.69 | | |

Example 21

This example reports the results of using a mixture of 2-Hydroxy-4-methoxy-benzophenone as the UV absorber (component A) and the diglycidyl ether of 1,4-butane as the organic epoxide (component B).

TABLE 22

| $Q_a$ | $Q_b$ | Δb Ratio (Experimental) | Δb Ratio (Calculated) | Synergy |
|---|---|---|---|---|
| 40 | — | 6.32 | | |
| 20 | 5 | 7.02 | 3.58 | yes |
| 20 | 10 | 15.26 | 3.96 | yes |
| 15 | 15 | 3.9 | 3.58 | yes |
| 15 | 20 | 6.75 | 3.98 | yes |
| 10 | 10 | 7.31 | 2.38 | yes |
| 10 | 20 | 15 | 3.19 | yes |
| — | 40 | 3.22 | | |

Example 22

This example reports the results of using a mixture of 2-Hydroxy-4-methoxybenzophenone as the UV absorber (component A) and Cresyl glycidyl ether as the organic epoxide (component B).

TABLE 23

| $Q_a$ | $Q_b$ | Δb Ratio (Experimental) | Δb Ratio (Calculated) | Synergy |
|---|---|---|---|---|
| 40 | — | 6.32 | | |
| 20 | 5 | 4.09 | 3.51 | yes |
| 20 | 10 | 5.98 | 3.86 | yes |
| 15 | 15 | 3.36 | 3.41 | no |
| 15 | 20 | 8.04 | 3.76 | yes |
| 10 | 10 | 4.51 | 2.28 | yes |
| 10 | 20 | 4.17 | 2.97 | yes |
| — | 40 | 2.78 | | |

Example 23

This example reports the results of using a mixture of 2-Hydroxy4-methoxybenzophenone as the UV absorber (component A) and trimethylol propane triglycidyl ether as the organic epoxide (component B).

TABLE 24

| $Q_a$ | $Q_b$ | Δb Ratio (Experimental) | Δb Ratio (Calculated) | Synergy |
|---|---|---|---|---|
| 40 | — | 6.32 | | |
| 20 | 5 | 3.81 | 3.50 | yes |
| 20 | 10 | 4.84 | 3.85 | yes |
| 15 | 15 | 3.44 | 3.40 | yes |
| 15 | 20 | 4.42 | 3.74 | yes |
| 10 | 10 | 2.76 | 2.27 | yes |
| 10 | 20 | 4.09 | 3.00 | yes |
| — | 40 | 2.75 | | |

Example 24

This example reports the results of using a mixture of 2-Hydroxy-4-methoxybenzophenone as the UV absorber (component A) and Araldite GY506 (supplied by Ciba-Geigy) as the organic epoxide (component B).

TABLE 25

| $Q_a$ | $Q_b$ | Δb Ratio (Experimental) | Δb Ratio (Calculated) | Synergy |
|---|---|---|---|---|
| 40 | — | 6.32 | | |
| 20 | 5 | 2.48 | 3.47 | no |
| 20 | 10 | 4.56 | 3.77 | yes |
| 15 | 15 | 3.9 | 3.29 | yes |
| 15 | 20 | 4.3 | 3.60 | yes |
| 10 | 10 | 3.51 | 2.19 | yes |
| 10 | 20 | 4.21 | 2.80 | yes |
| — | 40 | 2.45 | | |

Example 25

This example reports the results of using a mixture of 2-Hydroxy-4-methoxybenzophenone as the UV absorber (component A) and Aliphatic $C_{12}-C_{14}$ glycidyl ether (Araldite DY 025, supplied by Ciba-Geigy) as the organic epoxide (component B).

TABLE 26

| $Q_a$ | $Q_b$ | Δb Ratio (Experimental) | Δb Ratio (Calculated) | Synergy |
|---|---|---|---|---|
| 40 | — | 6.32 | | |
| 20 | 5 | 3.25 | 3.50 | no |
| 20 | 10 | 3.88 | 3.83 | yes |
| 15 | 15 | 3.4 | 3.38 | yes |
| 15 | 20 | 3.35 | 3.72 | no |
| 10 | 10 | 2.44 | 2.25 | yes |
| 10 | 20 | 2.48 | 2.92 | no |
| — | 40 | 2.69 | | |

While certain specific embodiments of the invention have been described with particularity herein, it will be recognized that various modifications thereof will occur to those skilled in the art and it is to be understood that such modifications and variations are to be included within the preview of this application and the spirit and scope of the appended claims.

We claim:

1. A stabilized biocidal composition comprising a mixture of a halopropynyl compound, a UV absorber and an organic epoxide, wherein an amount of said UV absorber and an amount of said organic epoxide are provided which synergistically stabilizes said halopropynyl compound, and wherein said organic epoxide has the formula:

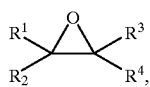

wherein $R^1$, $R^2$, $R^3$, and $R^4$ are independently selected from hydrogen; alkyl having 1–20 carbons; substituted alkyl; halogen; hydroxy; aryl; substituted aryl; alkoxy; alkoxyalkyl; 2,3-epoxy dialkoxyalkyl; aryl; aralkyl; aryloxy; aryloxyalky; alkanoyl;

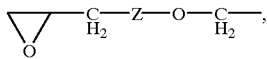

wherein Z is selected from the group consisting of straight or branched chain lower alkylene and halo-substituted lower alkylene; and

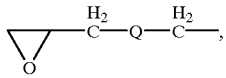

wherein Q is selected from the group consisting of alkylene having 1–4 carbon atoms and carbonylarylcarboxy;

or $R^1$ and $R^2$ or $R^2$ and $R^4$ may be joined together with the carbon atoms to which they are attached to form an alkylene chain of from 3 to 7 carbon atoms, which chain may be substituted with a lower alkylene to form a bicycloalkane or with a lower alkenyl radical;

wherein each of these groups may be further substituted with one or more additional epoxide groups.

2. The composition of claim 1 wherein the halopropynyl compound is selected from an iodopropynyl ester, an iodopropynyl ether, an iodopropynyl acetal, an iodopropynyl carbamate and an iodopropynyl carbonate.

3. The composition of claim 2 wherein the UV absorber is selected from benzotriazoles, benzophenones and substituted ethenes.

4. The composition of claim 3 wherein the halopropynyl compound is an iodopropynyl carbamate of the formula:

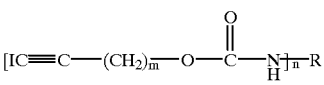

wherein R is selected from the group consisting of hydrogen, substituted and unsubstituted alkyl, aryl, alkylaryl, and aralkyl groups having from 1 to 20 carbon atoms and cycloalkyl and cycloalkenyl groups of 3 to 10 carbon atoms, and m and n are independent integers from 1 to 3.

5. The composition of claim 4 wherein the iodopropynyl carbamate is 3-iodo-2-propynylbutyl carbamate.

6. The composition of claim 5 wherein the UV absorber is a substituted ethene of the acrylate type or the benzylidene-camphor type.

7. The composition of claim 5 wherein the UV absorber is a benzotriazole.

8. The composition of claim 5 wherein the UV absorber is a benzophenone.

9. The biocidal composition of claim 6 wherein the UV absorber and the organic epoxide are present in a proportion of from about 1 part UV absorber to 9 parts organic epoxide to about 9 parts UV absorber to 1 part organic epoxide.

10. The biocidal composition of claim 7 wherein the UV absorber and the organic epoxide are present in a proportion of from about 1 part UV absorber to 9 parts organic epoxide to about 9 parts UV absorber to 1 part organic epoxide.

11. The biocidal composition of claim 8 wherein the UV absorber and the organic epoxide are present in a proportion of from about 1 part UV absorber to 9 parts organic epoxide to about 9 parts UV absorber to 1 part organic epoxide.

12. The biocidal composition of claim 1, 3, 5, 9, 10 or 11 containing from about 0.004% to 5.0% of said halopropynyl compound.

13. A paint containing the biocidal composition of claim 12.

14. A method for protecting a substrate from fungal infestation comprising coating said substrate with an effective amount of the paint of claim 13.

15. A stabilized biocidal composition comprising a mixture of a halopropynyl compound, a UV absorber and an organic epoxide, wherein an amount of said UV absorber and an amount of said organic epoxide are provided which synergistically stabilizes said halopropynyl compound, and wherein said organic epoxide is selected from the group consisting of a diglycidyl ether of 1,4-butanediol, cresyl glycidyl ether, trimethylol propane triglycidyl ether, and an aliphatic $C_{12}$–$C_{14}$ glycidyl ether.

16. The composition of claim 1 wherein $R^1$ is methyl, $R^3$ is hydrogen, and $R^2$ and $R^4$ are joined together with the carbon atoms to which they are attached to form a cyclohexene ring substituted with 1-methylethenyl or 2,3-epoxy propane.

17. The composition of claim 1 wherein $R^2$, $R^3$, and $R^4$ are hydrogen.

18. The composition of claim 17 wherein $R^1$ is substituted aryloxy.

19. The composition of claim 17 wherein $R_1$ is alkoxy.

20. The composition of claim 17 wherein $R^1$ is

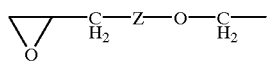

and Z is alkylene.

21. A stabilized biocidal composition comprising a mixture of a halopropynyl compound, a UV absorber, and an organic epoxide, wherein an amount of said UV absorber and an amount of said organic epoxide are provided which synergistically stabilizes said halopropynyl compound, and wherein said organic epoxide is selected from the group consisting of

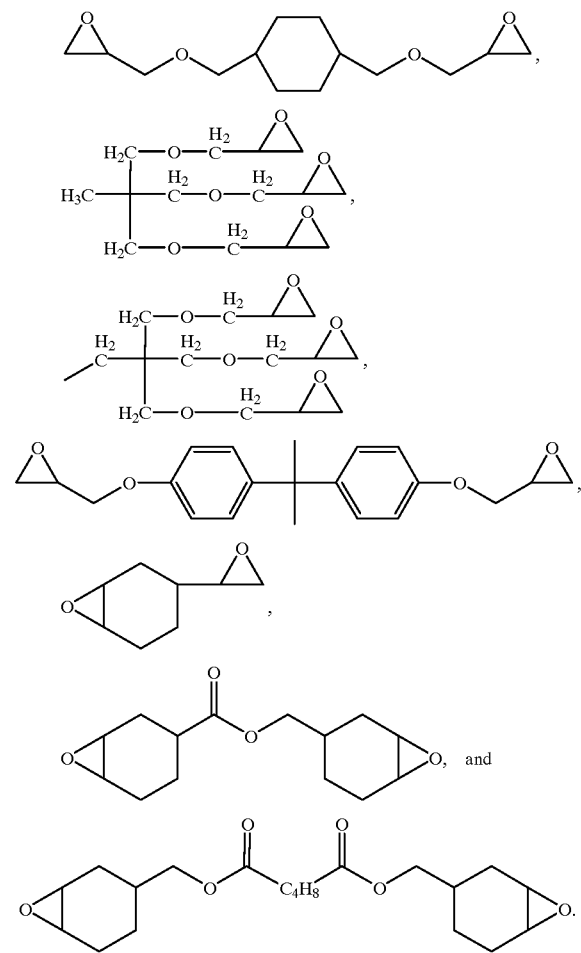

* * * * *